United States Patent [19]

Cook

[11] Patent Number: 5,026,428
[45] Date of Patent: Jun. 25, 1991

[54] MANUFACTURING PLASTER ARTICLES

[76] Inventor: Peter B. L. Cook, Fairfields House, Norwich Road, Horstead, Norwich, Norfolk, Great Britain, NR12 7EE

[21] Appl. No.: 292,680

[22] Filed: Jan. 3, 1989

[51] Int. Cl.$^5$ .......................... C04B 28/14; B28B 7/34
[52] U.S. Cl. ..................... 106/38.3; 106/35; 106/772; 106/783; 106/788
[58] Field of Search ............... 106/38.3, 109, 110, 106/35, 315, 772, 783, 788; 164/376

[56] References Cited

U.S. PATENT DOCUMENTS

| | | | |
|---|---|---|---|
| 3,042,537 | 7/1962 | Newell et al. | 106/109 |
| 3,083,110 | 3/1963 | Preston | 106/315 |
| 3,393,116 | 7/1968 | Larson et al. | 106/315 |
| 3,436,236 | 4/1969 | Gamber et al. | 106/38.3 |
| 3,520,708 | 7/1970 | Prytherch et al. | 106/315 X |
| 3,598,621 | 8/1971 | Ferrara et al. | 106/315 X |
| 4,148,660 | 4/1979 | Lankard et al. | 106/38.3 |
| 4,526,619 | 7/1985 | Ohi et al. | 106/109 X |
| 4,647,311 | 3/1987 | Ohi et al. | 106/109 X |

FOREIGN PATENT DOCUMENTS

| | | | |
|---|---|---|---|
| 4041933 | 4/1979 | Japan | 106/109 |

*Primary Examiner*—Karl Group
*Attorney, Agent, or Firm*—Neal J. Mosely

[57] ABSTRACT

In the production of plaster articles, for example, dental dies and moulds, powdered gypsum (calcium sulphate) is mixed with an aqueous solution of boric acid and/or silicic acid.

By incorporating boric acid and/or silicic acid in the mix, the hardness and setting characteristics of the mix are improved. In a typical application the concentration of boric acid in the aqueous solution is from 0.3 to 1.1 grams boric oxide per liter of solution and the preferred concentration of silicic acid in the aqueous solution is within the range of from 75 mls to 300 mls concentrated silicic acid per liter of aqueous solution.

12 Claims, No Drawings

MANUFACTURING PLASTER ARTICLES

FIELD OF THE INVENTION

This invention relates to the manufacture of articles from plaster, particularly dies and moulds used in dentistry and manufactured from plaster of paris.

DESCRIPTION OF THE PRIOR ART

Dental dies and moulds are conventionally prepared from plaster of paris, the production method involving mixing powdered gypsum with water, moulding the mix thus obtained to the required shape and causing or allowing the thus formed moulded shape to set.

SUMMARY OF THE INVENTION

According to one aspect of the present invention, there is provided a method of manufacturing a plaster article, which method includes mixing powdered calcium sulphate with a liquid, characterised in that the liquid is an aqueous solution of boric acid and/or silicic acid.

The powdered material which is mixed with the liquid may comprise solely calcium sulphate or, depending on the use to which the article is to be put and the strength and other requirements, other powdered materials may be incorporated in the powdered calcium sulphate. For example, powdered stone may be mixed with the calcium sulphate.

The aqueous solution preferably contains both boric acid and silicic acid with the result that, as the plaster solidifies, the crystal structure which is obtained contains both calcium borate and calcium silicate. By incorporating boric acid and/or silicic acid in the plaster, the amount of air entrapped in the powder is significantly reduced, the surface of a formed article is more resistant to abrasion and the article as a whole is both harder and stronger.

In patent specification (GB) 721,318 there is described a process for the production of a cementitious material from gypsum which involves the use of a dry powder mix containing alum and borax or boric acid plus anhydrite and to which a small quantity of sulphuric acid is added.

Patent specification No. 721,318 is concerned, however, with the production of products used in the building industry, for example, blocks and tiles and provides a powdered additive which is mixed with gypsum and to which water is then added.

In contrast therewith, the present invention is concerned with the use of an aqueous solution of boric acid and/or silicic acid, the concentrations of boric acid and silicic acid being selected so as to obtain the right hardness characteristics and setting characteristics facilitating the use of the method of the invention in the production of dental dies and moulds.

In a preferred application of the invention the rate of admixture of the aqueous solution to the calcium sulphate/gypsum is of the order of 7 mls. of the aqueous solution to 34 gms gypsum.

The preferred concentration of boric acid in the aqueous solution is within the range of from 0.3 gms boric oxide to 1.1 gms boric oxide per liter of solution. The preferred concentration of concentrated silicic acid in the aqueous solution is within the range of from 75 mls. to 300 mls concentrated silicic acid per liter of aqueous solution.

According to another aspect of the present invention, there is provided a mould or die for use in dentistry, which mould or die comprises a moulded and set mass formed by the mixing of powdered calcium sulphate with an aqueous solution of boric acid and/or silicic acid.

The setting time of the mixture is preferably of the order of fifteen to twenty minutes, thereby allowing sufficient time for working of the mix and formation of the required shape. As applied to a dental mould or die the mould or die will be usable in approximately two hours from the time of moulding and will reach its full strength in about twenty four hours.

DESCRIPTION OF THE PREFERRED EMBODIMENTS

Table A set out below shows a number of examples of the invention.

TABLE A

| Example | Boric Oxide | Water | Silicic Acid | Result |
|---|---|---|---|---|
| 1 | 1.1 gms | 840 ml | 160 ml | Set time over 40 mins. Good hardness after 48 hours. |
| 2 | 1.1 gms | 750 ml | 250 ml | Slower set. Good hardness after 48 hours |
| 3 | 0.9 gms | 845 ml | 155 ml | Set time 20 mins. Very good hardness |
| 4 | 0.75 gms | 850 ml | 150 ml | Set time 20 mins. Very good hardness |
| 5 | 0.3 gms | 925 ml | 75 ml | Set time 10 mins. Good hardness. |

In each instance the stated amount of boric oxide is dissolved in water and then the stated amount of a concentrated silicic acid solution is added to the boric acid solution, boric acid being produced when boric oxide is dissolved in water. The liquid is then used to produce a moulded object by mixing 34 gms of gypsum with 7 mls of the liquid and expansion and hardness tests are carried out in accordance with the requirements of international standard ISO 6873.

These are four types of gypsum products used in dentistry, the different products being classified by the International Standards Organisation as follows:

Type 1—Impression Plaster
Type 2—Plaster
Type 3—Stone
Type 4—Stone (high strength)

The method of the present invention is applicable to each type of gypsum product referred to above. In addition, although the invention has been developed in relation to the production of dental moulds and dies, the invention is not limited to such dental applications.

By using an aqueous solution of boric acid and silicic acid in place of water alone, certain advantages are obtained. Such advantages include the following:

1. An increase in hardness of the mixed and set mass, for example, after mixing and allowing to set for one hour, an increase in hardness is obtained of between 8 and 16% as compared to mixing the same plaster material with water alone, 2. The setting expansion co-efficient of the gypsum is maintained within the requirements specified by the International Standards Organisation, 3. Less air is entrapped in the mix thus ensuring the production of a denser, more consistent mass as compared with the same plaster materials mixed with water alone, 4. When the solution of boric acid and silicic acid is mixed with the plaster, the initial mixture has thixotropic properties, thereby preventing running and dripping of the mixed mass in an uncontrolled manner, 5. The heat generated by the exothermic reaction that occurs with plaster materials when mixed with water is very much reduced, thus improving the dimensional stability of a moulded product and reducing the risk of distortion which can be caused by the exothermic reaction, 6. The fine-edge strength of a moulded product is increased as a result of the increase in density and hardness of the moulded product.

Of the specific examples referred to above, example 4 gives the best all round results for use with types 1 to 4 dental plasters, the optimum setting time being of the order of 12 to 15 minutes. It is possible to use a more dilute solution than that of example 5 but, with such more dilute solutions, the increase in hardness which is obtained is reduced. If the concentration of silicic acid is increased, a reduction in the workability of the mix is obtained. It is accordingly preferred that the silicic acid content should not exceed 300 mls per liter of solution. When the amount of boric acid is increased, an increase in the set time is obtained and it is accordingly preferred that the amount of boric oxide should not exceed 1.2 gms per liter of solution. The solution may be supplied to dental technicians at the concentrations specified above. Alternatively, the solution may be provided in more concentrated form, together with instructions as to how it should be diluted.

The inclusion of the boric acid and the silicic acid in the liquid with which the gypsum is mixed results in the formation of a crystal structure in which calcium borate and calcium silicate are interspersed with calcium sulphate and it is this incorporation of the borate and the silicate that results in the improved strength, consistency and abrasion resistance characteristics of a moulded article.

The powdered mix to which the liquid is added need not be calcium sulphate alone; other powdered or particulate refractory materials may be incorporated in the plaster mix, the use of such additives being determined by the strength and other characteristics which are required for the finished moulded article.

I claim:

1. A method of manufacturing a plaster article, which method comprises
    forming an aqueous solution from boric oxide and concentrated aqueous silicic acid, said solution consisting of a homogeneous solution of boric acid and silicic acid,
    mixing a selected amount of said homogeneous solution of boric acid and silicic acid with powdered calcium sulfate to produce a thixotropic composition which sets in 12-15 minutes to a workable form,
    forming said thixotropic composition into an article, and
    allowing said article to set for at least two hours to a usable form.

2. A method according to claim 1, in which
    the rate of admixture of said homogeneous solution to said calcium sulfate is in the proportion of about 7 mls of the homogeneous solution to 35 gms of the calcium sulfate.

3. A method according to claim 1, in which
    the concentration of boric acid in said homogeneous solution is within the range of from 0.3 gms boric oxide to 1.0 gms boric oxide per liter of solution.

4. A method according to claim 1, in which
    the concentration of silicic acid in said homogeneous solution is within the range of from 75 mls to 300 mls concentrated silicic acid per liter of aqueous solution.

5. A method according to claim 1, in which
    the concentration of boric acid in said homogeneous solution is within the range of from 0.3 gms boric oxide to 1.0 gms boric oxide per liter of solution, and
    the concentration of silicic acid in said homogeneous solution is within the range of from 75 mls to 300 mls concentrated silicic acid per liter of aqueous solution.

6. A method according to claim 1, in which
    the concentration of boric acid in said homogeneous solution is within the range of from 0.3 gms boric oxide to 1.0 gms boric oxide per liter of solution,
    the concentration of silicic acid in said homogeneous solution is within the range of from 75 mls to 300 mls concentrated silicic acid per liter of aqueous solution, and
    the rate of admixture of said homogeneous solution to said calcium sulfate is in the proportion of about 7 mls of the homogeneous solution to 35 gms of the calcium sulfate.

7. A mold or die for use in dentistry formed according to claim 1 characterized by having working strength after two hours and full strength after 24 hours.

8. A mold or die for use in dentistry formed according to claim 2 characterized by having working strength after two hours and full strength after 24 hours.

9. A mold or die for use in dentistry formed according to claim 3 characterized by having working strength after two hours and full strength after 24 hours.

10. A mold or die for use in dentistry formed according to claim 4 characterized by having working strength after two hours and full strength after 24 hours.

11. A mold or die for use in dentistry formed according to claim 5 characterized by having working strength after two hours and full strength after 24 hours.

12. A mold or die for use in dentistry formed according to claim 6 characterized by having working strength after two hours and full strength after 24 hours.

* * * * *